United States Patent [19]

Chrisope

[11] Patent Number: 5,279,964
[45] Date of Patent: Jan. 18, 1994

[54] STORABLE INOCULATION DEVICE CONTAINING STABILIZED MICROORGANISMS

[75] Inventor: Gerald L. Chrisope, Sulphur, La.

[73] Assignee: Chrisope Technologies, Inc., Lake Charles, La.

[21] Appl. No.: 789,768

[22] Filed: Nov. 8, 1991

Related U.S. Application Data

[63] Continuation of Ser. No. 588,484, Sep. 21, 1990, abandoned, which is a continuation of Ser. No. 401,525, Aug. 28, 1989, abandoned, which is a continuation of Ser. No. 34,438, Apr. 3, 1987, abandoned, which is a continuation of Ser. No. 569,677, Jan. 10, 1984, abandoned.

[51] Int. Cl.$^5$ ............................................. C12M 1/26
[52] U.S. Cl. ............................ 435/292; 435/287; 435/810
[58] Field of Search ............... 435/29, 30, 32, 33, 435/243, 260, 287, 292, 293, 810; 128/759; 604/1

[56] References Cited

U.S. PATENT DOCUMENTS

| | | | |
|---|---|---|---|
| 2,738,273 | 3/1956 | Muhrer | 435/260 |
| 2,908,614 | 10/1959 | Muggelton et al. | 435/260 |
| 3,077,780 | 2/1963 | Takatsy . | |
| 3,147,197 | 9/1964 | Connors | 435/292 |
| 3,168,796 | 2/1965 | Scott et al. | 435/810 |
| 3,191,813 | 6/1965 | Duff . | |
| 3,255,494 | 6/1966 | Bloch et al. | 604/1 |
| 3,282,114 | 11/1966 | Pell . | |
| 3,455,788 | 7/1969 | Curry et al. | 435/293 |
| 3,632,478 | 1/1972 | Fink . | |
| 3,671,400 | 6/1972 | Cekoric, Jr. et al. | 435/810 |
| 3,742,187 | 6/1973 | Folus . | |
| 3,843,456 | 10/1974 | Haden et al. | 435/810 |
| 3,875,015 | 4/1975 | Wadley et al. . | |
| 3,915,806 | 10/1975 | Horlach | 435/292 |
| 4,010,077 | 3/1977 | Pardos | 435/294 |
| 4,018,222 | 4/1977 | McAleer et al. | 604/113 |
| 4,102,748 | 7/1978 | Vacanti . | |
| 4,234,316 | 11/1980 | Hevey | 435/810 |
| 4,242,462 | 12/1980 | Thomas . | |
| 4,275,031 | 6/1981 | Fischer | 435/810 |
| 4,330,627 | 5/1982 | Thomas et al. | 435/301 |
| 4,529,702 | 7/1985 | Bryan | 435/260 |

FOREIGN PATENT DOCUMENTS 0684065 9/1979 U.S.S.R. .......................... 435/287

*Primary Examiner*—Robert J. Warden
*Assistant Examiner*—T. A. Trembley
*Attorney, Agent, or Firm*—Browning, Bushman, Anderson & Brookhart

[57] ABSTRACT

The present invention is directed to an inoculation device including an easily manipulated handle together with microorganisms associated with a device for transferring and storing for extending periods stabilized, known microorganisms. This device is particularly useful in testing standard laboratory culture media. This device is easily produced by associating known microorganisms, either alone or together with a binding agent and other biologically acceptable additives and preservatives, with the sample transfer portion of the inoculation device. When substantially all of the water is removed from an inoculation device, including known microorganisms, the microbial containing device is storable for extended periods under sterile, dry conditions substantially free of water. The present method and apparatus conveniently and economically produces a disposable standard inoculation device useful by clinical laboratories in storing and transferring microorganisms to various growth media for testing or cell maintenance programs.

20 Claims, 1 Drawing Sheet

U.S. Patent    Jan. 18, 1994    5,279,964
FIG. 1
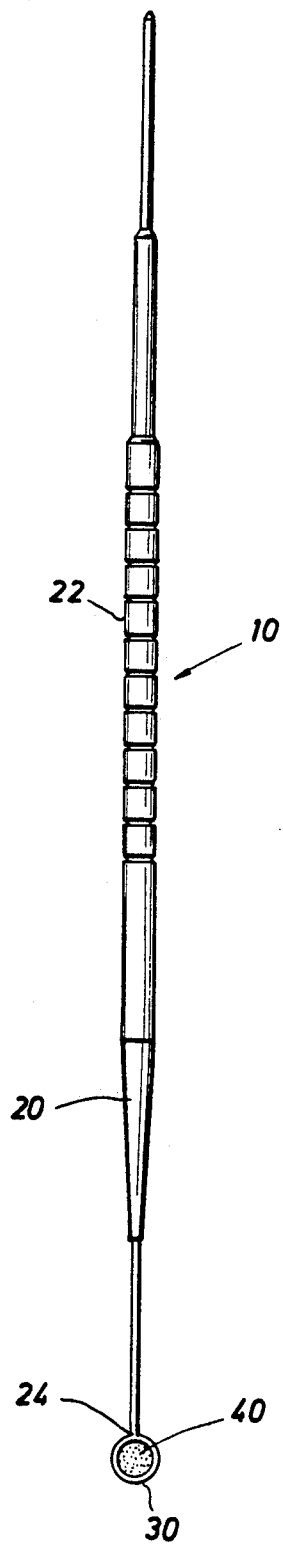
FIG. 2
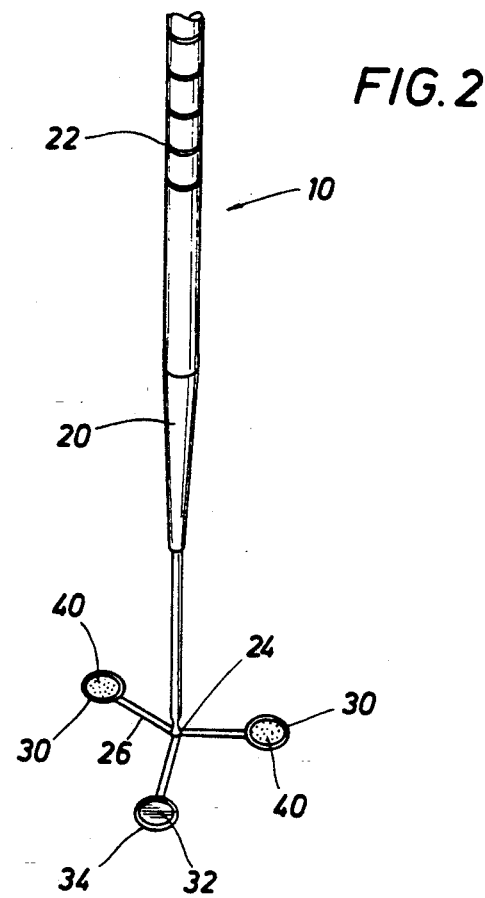
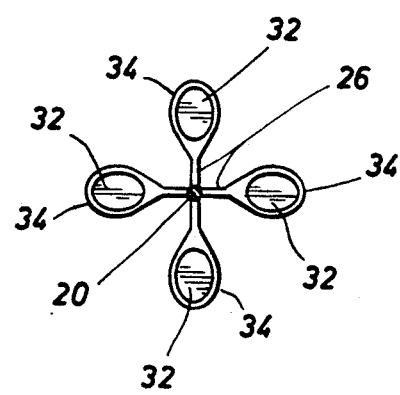
FIG. 3

STORABLE INOCULATION DEVICE CONTAINING STABILIZED MICROORGANISMS

This is a continuation of U.S. application Ser. No. 07/588,484 filed Sep. 21, 1990, which is a continuation of U.S. application Ser. No. 07/401,525 filed Aug. 28, 1989, which is a continuation of application Ser. No. 07/034,438 filed Apr. 3, 1987, which is a continuation of application Ser. No. 06/569,677 filed Jan. 10, 1984, now all abandoned.

BACKGROUND OF THE INVENTION

1. Field of the Invention

The present invention generally relates to a transfer and inoculation device useful for transferring, including storage for extended periods, of microorganisms to laboratory growth media. The present invention is particularly useful for testing the quality of a variety of laboratory growth media. More particularly, the present invention relates to a storable, inoculation device including one or more known, stabilized microorganisms and a method of producing, stabilizing and storing the same.

2. Description of the Background

Various culture media are routinely used in the growth of specimens in standard diagnostic procedures by laboratories engaged in providing microbiological analyses. A typical clinical laboratory employs a variety of different media types with each specimen submitted for examination. For example, a submitted specimen is often initially inoculated onto agar plates and, after an initial incubation, individual microorganism types are separated and identified using additional growth media. These methods are used routinely in making diagnostic predictions relating to many infections.

In performing these tests, the quality and state of the various culture media must be maintained. Further, clinical laboratories are required by various regulatory and certifying agencies to routinely subject samples of media to quality control evaluation. This testing must be performed on all culture media, whether the media is commercially purchased or is prepared by the facility. The frequency of testing varies from daily testing to random testing of individual lots.

For these quality control tests, appropriate microorganisms are cultured on the growth medium sample. After a prescribed inoculation period, often about 24 hours to 48 hours, at a prescribed temperature, generally about 35° C., the growth patterns of the inoculated microorganisms are observed. These growth patterns may be observed merely qualitatively and the medium approved or disapproved based comparison to expected results. Alternatively, growth patterns may be studied more closely for quantitative analysis prior to approval of the medium.

The testing methods generally employed are conventional and known to those in the art. However, in summary, the microorganism to be used in the test is often cultured in a broth tube overnight. Microorganisms are transferred from the broth to the surface of the medium to be tested using a standard, sterile inoculation loop. For example, plastic disposable loops or reusable metal loops which have been heat-sterilized by flame or electric heating are generally employed. The inoculated media is incubated at a prescribed temperature, often 35° C., for a prescribed time, generally about 24–48 hours. In a qualitative test, the microbial growth resulting from this procedure is simply observed and characterized as either typical or atypical. In quantitative testing, a known quantity of microorganisms prepared by dilution from the broth is placed in the medium to be tested by the above transfer procedure. After the prescribed incubation period, comparative culture counts are made.

These testing procedures require that the test microorganisms be viable and that the microorganisms maintain similar characteristics from generation to generation. Many laboratories maintain a supply of testing microorganisms by continually subculturing derived from the original microorganisms. However, this repeated subculturing is time-consuming and costly. But, more importantly, repeated subculturing often leads to the eventual loss of some of the original characteristics of the microorganism. Further, some microorganisms have relatively short lives and must repeatedly be subcultured, often once a day, presenting a drain on the resources and time of the laboratory. In summary, the subculturing of test microorganisms simply results in the unnecessary expenditure of laboratory resources and time, together with an increased chance for the production of mutated cultures.

Lyophilization and dessication techniques for preserving bacteria have been known for decades. In fact, a variety of strains of lyophilized bacteria useful for testing purposes are available commercially. These products generally comprise resealable storage bottles or vials containing small discs of gelatin and charcoal containing the desired bacteria. These discs are removed from the vial or storage bottles and used to directly or indirectly inoculate a growth medium or broth as described above.

The culturing and subculturing of inoculation microorganisms is undesirable for the reasons stated above. Further, the commercially available discs are difficult to handle, requiring aseptic manipulation by tweezers or tongs and the like.

The improved inoculation device of the present invention provides an easily manufactured, easily stored and easily manipulated device. Such a device contains one or more known, stabilized microorganisms for accurate and easy inoculation of growth media for testing purposes.

SUMMARY OF THE INVENTION

The present invention provides a new and improved transfer and inoculation device including stabilized microorganisms affixed directly thereon. Such devices survive extended storage in sterile containers substantially free from water to provide viable microorganisms for use in testing procedures.

An inoculation device in accord with the present invention comprises a handle having attached thereto means for temporarily holding during transfer stabilized microorganisms and the stabilized, known microorganisms associated therewith. Any desired microorganism such as procraytoes or eucraytses may be associated therewith. Preferably, a biologically acceptable binding agent, such as a water-soluble gum, is employed to aid in temporarily affixing the microorganisms to the transfer means. Further, any desirable, biologically acceptable additive or preservative is optionally associated therewith. For example, certain carbohydrates, proteins, reducing agents, toxin neutralizing agents and cryoprotective agents are optionally included in association with the transfer means. The device, including the microorganisms and associated materials, is lyophilized or dessicated to remove substantially all of the water therefrom. An inoculation device containing stabilized microorganisms in accord with the present invention is storable for extended periods in a sterile container substantially free from water. These containers optionally include a dessicant. These containers may be resealable for repeated use or may be disposable, such as metallic foil packages for single devices.

In an alternative embodiment, each inoculation device includes a plurality of transfer means attached to a single handle. This alternative device is readily employed for storage of a plurality of different microorganisms, each microorganism associated with a separate holding means, to produce an inoculation device capable of initiating separate growth of a plurality of different microorganisms on a test medium.

A presently preferred method of producing a storable inoculation device in accord with the present invention comprises contacting known microorganisms in a biologically acceptable carrier solution with the sample transfer means of a hand-held inoculation device. The method further comprises stabilizing the affixed microorganisms by removing substantially all of the water therefrom and storing the device, including the microorganisms, in a sterile, dry atmosphere in a container substantially free of water. Such devices have been stored in conventional freezers, refrigerators or even on the laboratory shelf for extended periods until later use is desired.

The device and method of the present invention provides an easily manufactured, stored and used inoculation device containing known, stabilized microorganisms particularly useful in the testing of various growth media.

BRIEF DESCRIPTION OF THE DRAWINGS

Other features and intended advantages of the invention will be more readily apparent by the references to the following detailed description in connection with the accompanying drawings wherein:

FIG. 1 is a side view of an inoculation device of the present invention;

FIG. 2 is a perspective view of an inoculation device of an alternate embodiment of the present invention; and FIG. 3 is a top view of another alternate inoculation device of the present invention.

While the invention will be described in connection with a presently preferred embodiment and several alternate embodiments, it will be understood that it is not intended to limit the invention to these embodiments. On the contrary, it is intended to cover all alternatives, modifications and equivalents as may be included within the spirit of the invention as defined in the appended claims.

DETAILED DESCRIPTION OF THE PREFERRED EMBODIMENTS

The drawings illustrate several embodiments of the present invention wherein like reference numerals identify like parts.

FIG. 1 of the drawings illustrates inoculation device 10 in accord with the present invention. Inoculation device 10 comprises an easily manipulated handle 20. The illustrated device includes ribs 22 on handle 20 to aid in gripping the handle. Attached at 24 to handle 20 is transfer means such as loop 30. Preferably, handle 20 is integral with loop 30 as illustrated so that inoculation device 20 is simply of a unitary construction. The transfer means may take any desired shape and construction. For example, inoculation device 10 of FIG. 2 comprises three (3) transfer means, including both open loops 30 and relatively flat disc 32 having raised rim 34 thereabout, both types attached to arms 26. Any device with which microorganisms may be transferred or temporarily affixed is satisfactory. In the embodiment of FIG. 2, a thin film 40 comprising the binding agent, gelatin and the known microorganisms is evident spanning loop 30. FIG. 3 illustrates another embodiment of an inoculation device in accord with the present invention having four (4) solid transfer discs 32, including raised rims 34 attached to arms 26 spaced at relatively equal intervals about one end of handle 20. Handle 20 may be permanently and fixedly attached to arms 26 at 24 or may be attached by any appropriate hinge means, such as a polypropylene hinge to provide a flat and more readily storable device. Alternatively, handle 20 may be reusable and designed for easy engagement and disengagement at 24 from disposable arms and transfer means by a variety of means known to those skilled in the art.

In the presently preferred embodiments, the inoculation devices, including the handle and transfer means, are constructed of any appropriate, sterilizable and biologically acceptable material. For example, polystyrene, polypropylene, other plastics and even wood products, such as chip board, are easily and economically employed to produce disposable inoculation devices.

A convenient means for preparing standard inoculation devices in accord with the present invention begins with the preparation of a variety of reagent solutions for containing the viable microorganisms to be deposited onto the device. Any procedure acceptable for the production and transfer of microorganisms may be employed. One such procedure is outlined by Obara, et al at pages 61–66 of Volume 14 of the *Journal of Clinical Microbiology* (1981).

In a presently preferred method of production, a first solution containing about five percent (5%) carbohydrate, about three percent (3%) protein and optionally about 0.6 percent (0.6%) of a toxin neutralizing agent is prepared in water. The carbohydrate of preference is dextrose, although any other suitable, simple carbohydrate may be employed. Protein is preferably supplied in the form of albumin or even skim milk. Powdered charcoal provides an acceptable and readily available toxin neutralizing agent. A second solution comprises about twenty percent (20%) gelatin or other biologically acceptable protein in water. A final solution containing about five percent (5%) sodium ascorbate or another biologically acceptable reducing agent is prepared in water. The above solutions are combined, preferably in an appropriate ratio of 1:1:0.2. To the resulting solution is added a biologically acceptable binding or adhesive agent, such as a cold, water-soluble gum. Further, more stable long-term storage under cryogenic conditions is obtained by use of appropriate preservatives. Compounds including an amino group, a secondary alcohol group, or both, provide excellent preservatives. Preservatives are conveniently selected from the polyols, alcohols, compound with amino groups, salts of organic acids and various other compounds producing the desired physico-chemical protective results. Glycerol and adonitol are excellent preservatives for many microorganisms. Finally, viable, known microorganisms are harvested from appropriate growth media such as agar plates, broth, tissue culture media and the like and suspended in the above solution.

The presently preferred method of producing standard inoculation devices in accord with the present invention comprises contacting the reagent prepared as described above with a loop, plate or other transfer means of an appropriate inoculation device including an easily manipulated handle. This contact results in the transfer of a portion of the solution, including the known microorganisms to the holding means. The standard inoculation device, including the transferred solution, is treated to remove substantially all of the carrier solution or liquid therefrom. This stabilization is preferably achieved by dessication, although lyophilization may also be employed. Inoculation devices, including stabilized microorganisms, produced in accord with the present invention are readily stored for later use in a dry, sterile container substantially free of water. Storage has been in a standard freezer, refrigerator or even on an open shelf. Inoculation devices produced and stored in accord with the present invention have been found to have a reliable shelf life exceeding six (6) months. It is believed that when these devices are properly produced and stored the shelf life would theoretically be indefinite.

Standard inoculation devices produced in accord with the present invention are easily stored in individual packages impermeable to water, such as metallic foil packaging commonly known to those skilled in the art of packaging. Alternatively, a plurality of inoculation devices produced in accord with the present invention are stored together in a resealable jar or other container, preferably including a dessicant to prevent deterioration of the remaining devices from water vapor entering the container during opening thereof. These devices are conveniently transported and stored for extended periods prior to opening and use. The present invention produces desirable, low cost and disposable standard inoculation devices.

In alternative embodiments such as those illustrated in FIGS. 2 and 3, a standard inoculation device in accord with the present invention comprises a plurality of transfer means, each of which may have a different microorganism easily associated therewith. These devices are useful for inoculating a test media with a plurality of different organisms.

When employing a standard inoculation device of the present invention for qualitatively testing a growth medium, the inoculation device, after removal from the storage means, is directly used to streak the medium to be tested. Alternatively, the device is employed to produce a suspension fluid, a portion of which is transferred to the medium for quantitative testing.

The standard inoculation device of the present invention is highly advantageous in that it eliminates the time, expense and chance for mutation and contamination associated with the typical laboratory subculturing of testing microorganisms. Accordingly, laboratories employing the standard inoculation device of the present invention will save valuable laboratory time and expense. Further, laboratory space and culture media will be saved by eliminating the need to maintain standard testing microorganisms.

The foregoing description of the invention has been directed in primary part to a particular preferred embodiment and method in accordance with the requirements of the patent statutes and for purposes of explanation and illustration. It will be apparent, however, to those skilled in the art that many modifications and changes in the specifically described apparatus and method may be made without departing from the scope and spirit of the invention. For example, any biologically acceptable additive or preservative may be included with the transferred microorganism. Further, the present invention produces a convenient device for storing microorganisms for easy handling and transfer to growth media at a later date or location. Therefore, the invention is not restricted to the particular form of construction and method illustrated and described, but covers all modifications which may fall within the scope of the following claims.

It is Applicant's intention in the following claims to cover such modifications and variations as fall within the true spirit and scope of the invention.

What is claimed is:

1. The combination of an inoculation device and a storage container, comprising:
   (1) a disposable inoculation device useful for storing and transferring known microorganisms to growth media, comprising:
      a rigid, plastic handle having grip means disposed along at least a portion of said rigid, plastic handle to aid in gripping and manipulating said disposable inoculation device;
      plastic loop means for storing and transferring viable microorganisms, said plastic loop means disposed at one end of said handle and integral with said rigid plastic handle;
      a film of a biologically acceptable, water-soluble binding agent, said film spanning said plastic loop means;
      stabilized, known microorganisms affixed in said film of a biologically acceptable, water-soluble binding agent; and
      a biologically acceptable preservative for said stabilized, known microorganisms disposed in said film; and
   (2) a disposable storage container, comprising:
      a dessicant;
      a sterile atmosphere substantially free from water; and
      a metallic foil package for enclosing and storing said disposable, inoculation device and dessicant in said sterile atmosphere.

2. The combination of claim 1 wherein said grip means comprises ribs disposed along said rigid plastic handle.

3. The combination of claim 1 wherein said biologically acceptable, water-soluble binding agent is a water-soluble gum.

4. The combination of claim 3 wherein said biologically acceptable preservative is selected from the group consisting of dextrose, gelatin, albumin, skim milk, sodium ascorbate, powdered charcoal, polyols, alcohols, compounds with amino groups, and salts of organic acids.

5. The combination of claim 4 wherein said polyols are selected from the group consisting of glycerol and adonitol.

6. The combination of claim 1 wherein said biologically acceptable preservative is selected from the group consisting of carbohydrates, proteins, reducing agents, toxic neutralizing agents and cryoprotective agents.

7. The combination of claim 6 wherein said stabilized, known microorganisms are selected from the group consisting of procaryotic microorganisms and eucaryotic microorganisms.

8. The combination of claim 1 wherein a plurality of said plastic loop means are integrally disposed at said one end of said rigid, plastic handle.

9. The combination of claim 8 wherein each said plastic loop means has affixed thereto stabilized, known microorganisms different from those affixed to each other said plastic loop means.

10. The combination of claim 1 wherein said plastic loop means is spanned by a disc upon which said film and said stabilized, known microorganisms are disposed.

11. The combination of an inoculation device and storage container, comprising:
(1) a disposable inoculation device useful for storing and transferring known microorganisms to growth media, comprising:
a rigid handle;
loop means for storing and transferring viable microorganisms, said loop means disposed at one end of said rigid handle in a plane substantially perpendicular to the axis of said rigid handle;
a film of a biologically acceptable, water-soluble binding agent, said film spanning said loop means; and
stabilized, known microorganisms affixed in said film of a biologically acceptable, water-soluble binding agent; and
(2) a disposable storage container, comprising:
a sterile atmosphere substantially free from water; and
a disposable package for enclosing and storing said disposable, inoculation device in said sterile atmosphere.

12. The combination of claim 11 wherein said disposable inoculation device further comprises a plurality of said loop means, each of said loop means disposed in said plane substantially perpendicular to the axis of said rigid handle.

13. The combination of claim 12 wherein each said loop means has affixed thereto stabilized, known microorganisms different from those affixed to each other said loop means.

14. The combination of claim 13 further comprising a plurality of arms, one said arm interposed in said plane between each said loop means and said rigid handle.

15. The combination of claim 12 wherein said disposable inoculation device further comprises a biologically acceptable preservative for said stabilized, known microorganisms dispersed in said film and said disposable storage container further comprises a dessicant.

16. The combination of claim 12 wherein said rigid handle and loop means are plastic and said handle further comprises grip means disposed along at least a portion of said rigid handle to aid in gripping and manipulating said disposable inoculation device.

17. The combination of claim 12 wherein said plurality of loop means are disposed substantially symmetrically about said rigid handle in said plane.

18. The combination of an inoculation device and storage container, comprising:
(1) a disposable inoculation device useful for storing and transferring known microorganisms to growth media, comprising:
a rigid handle;
loop means for storing and transferring viable microorganisms, said loop means disposed at one end of said rigid handle and integral with said rigid handle;
a film of a biologically acceptable, water-soluble binding agent, said film spanning said loop means; and
stabilized, known microorganisms affixed in said film of a biologically acceptable, water-soluble binding agent; and
(2) a disposable storage container, comprising:
a dessicant;
a sterile atmosphere substantially free from water; and
a package for enclosing and storing said disposable inoculation device and desiccant in said sterile atmosphere.

19. The combination of claim 18 wherein said disposable inoculation device further comprises a biologically acceptable preservative for said stabilized, known microorganisms dispersed in said film and said package for storing said disposable inoculation device comprises a metallic foil.

20. The combination of claim 19 wherein said rigid handle and loop means are plastic and said rigid handle further comprises grip means disposed along at least a portion of said handle to aid in gripping and manipulating said disposable inoculation device.

* * * * *